United States Patent [19]

Pailer et al.

[11] 4,242,360

[45] Dec. 30, 1980

[54] CHOLERETIC PHARMACEUTICAL COMPOSITIONS AND METHOD OF TREATMENT

[75] Inventors: Mathias Pailer, Vienna, Austria; Roland Wagner, Bergisch-Gladbach, Fed. Rep. of Germany

[73] Assignee: Rowa Limited, Cork, Ireland

[21] Appl. No.: 971,403

[22] Filed: Dec. 20, 1978

[30] Foreign Application Priority Data

Dec. 23, 1977 [DE] Fed. Rep. of Germany ....... 2757641

[51] Int. Cl.³ ........................................... A61K 31/045
[52] U.S. Cl. .................................................... 424/343
[58] Field of Search ......................................... 424/343

[56] References Cited

U.S. PATENT DOCUMENTS

| | | | |
|---|---|---|---|
| 3,075,881 | 1/1963 | Nordmann | 424/343 |
| 3,183,151 | 5/1965 | Nordmann | 424/343 |

*Primary Examiner*—Frederick E. Waddell
*Attorney, Agent, or Firm*—Bacon & Thomas

[57] ABSTRACT

Pharmaceutical choleretic compositions as well as methods of treatment for increasing choleresis and reducing the cholesterol content of the bile fluid are disclosed wherein cis-3,3,5-trimethylcyclohexanol is used as active choleretic ingredient.

3 Claims, 4 Drawing Figures

CHOLERETIC PHARMACEUTICAL COMPOSITIONS AND METHOD OF TREATMENT

DESCRIPTION

The subject of the patent is the preparation of a drug with a high choleretic effect and good tolerance for the treatment of biliary disorders.

It has surprisingly been shown that the isomer cis-(3,3,5)-Trimethylcyclohexanol is highly effective in the formation of bile. Therefore this substance is extremely suitable for the treatment of biliary disorders.

The subject of the patent is the use of cis-(3,3,5)-Trimethylcyclohexanol for the treatment of biliary disorders.

The therapeutical application can take the form of tablets, capsules, sugar-coated pills, suppositories, rectal capsules or a solution for injection.

Preliminary tests on rats were conducted to prove the therapeutic efficacy of the substance cis-(3,3,5)-Trimethylcyclohexanol. The substance was administered orally and the changes in the flow of bile were measured. The investigations were carried out in accordance with the test method of Boucard (Therapie 21,903, 1966). After the preparation of the bile duct, the bile which formed was measured every 30 minutes. In each case the substance was administered orally after the lapse of 60 minutes. The quantity of bile which formed was measured at further intervals of 30 minutes over a total period of 3 hours. The measurements were carried out on a group of control animals, which received peanut oil on a group to which a comparable substance was given, and on three groups to which the substance which is the subject of the invention was administered in varying doses. In each case the volume of bile flow, the cholesterol content and the dry weight of the bile fluid was determined.

Figure 1:
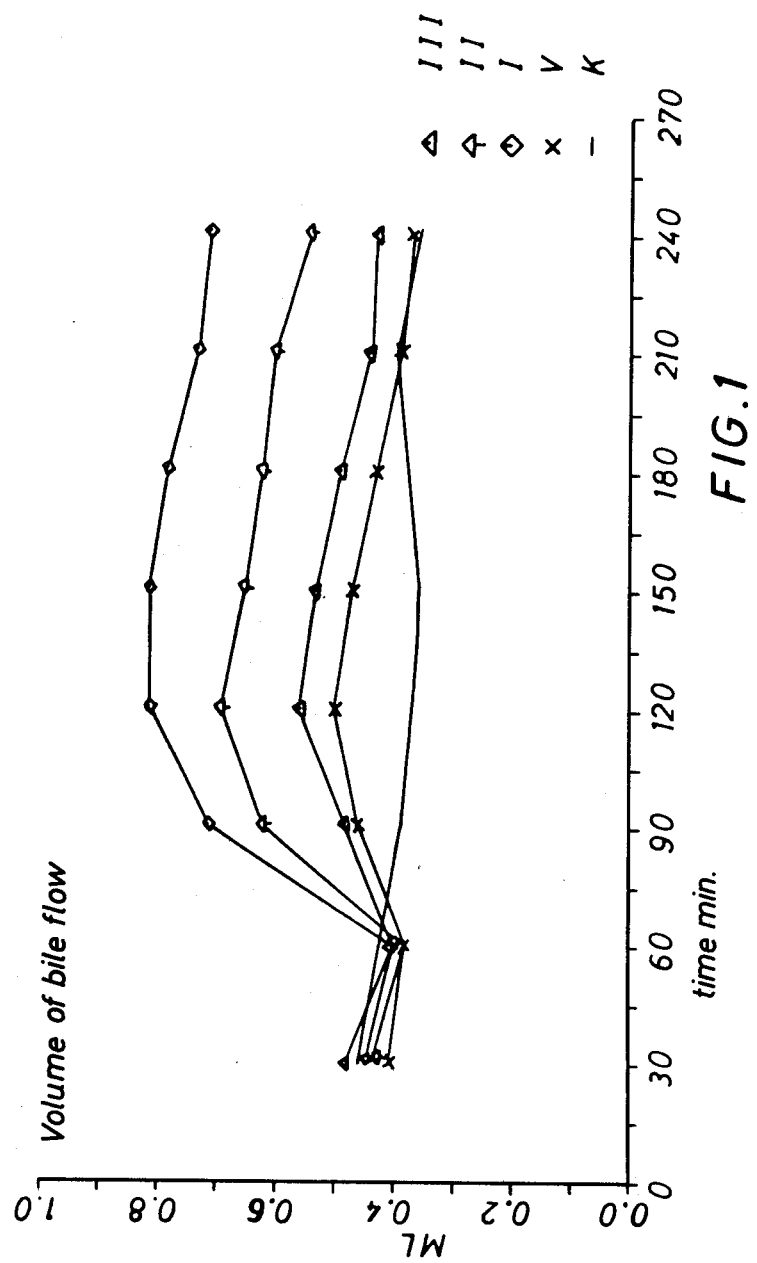

FIG. 1 shows the measured values for the volume of bile flow. These figures are for a control group K, a comparison group V and for three test groups I, II, III, to which the substance which is the subject of the invention was administered on a decreasing scale of dosage. The time scale begins with the time when the bile duct was prepared. The flow of bile was measured at 30 minutes and 60 minutes after this time. At the end of the 60-minute period the respective substances were administered. The measurements were then carried out for 3 hours at intervals of 30 minutes.

In the test groups I and II (which received a dosage of 0.3 ml/kg and 0.15 ml/kg respectively of cis-(3,3,5)-Trimethylcyclohexanol) it was found that the volume of bile increased to a high degree compared to the control group. The significance of the measured values was checked by the variance analysis method, using the Tuckey test. The substance which is the subject of the invention achieved its maximum effect at 60 and 90 minutes after administration.

Figure 2:
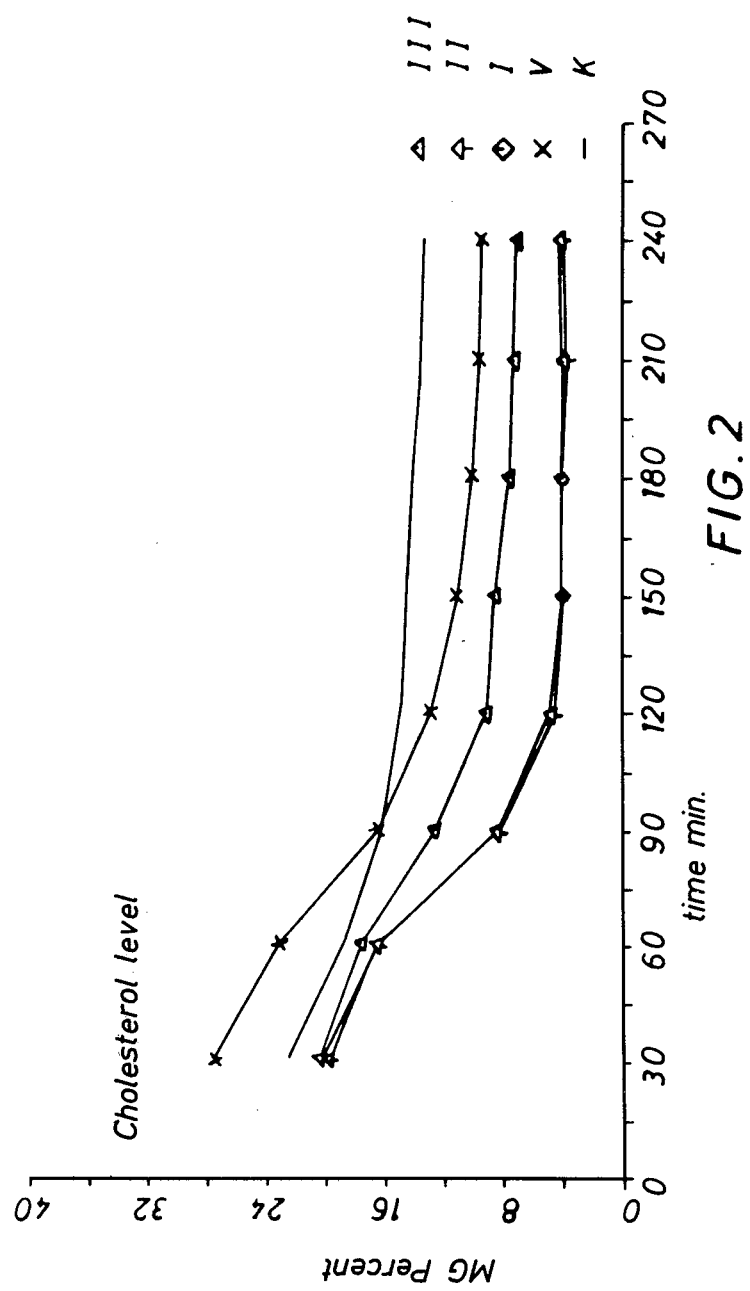

FIG. 2 shows the corresponding measurements of the cholesterol level. The Test groups I and II show a highly significant reduction of the cholesterol figures as compared to the control group K and the comparison group V.

Figure 3:
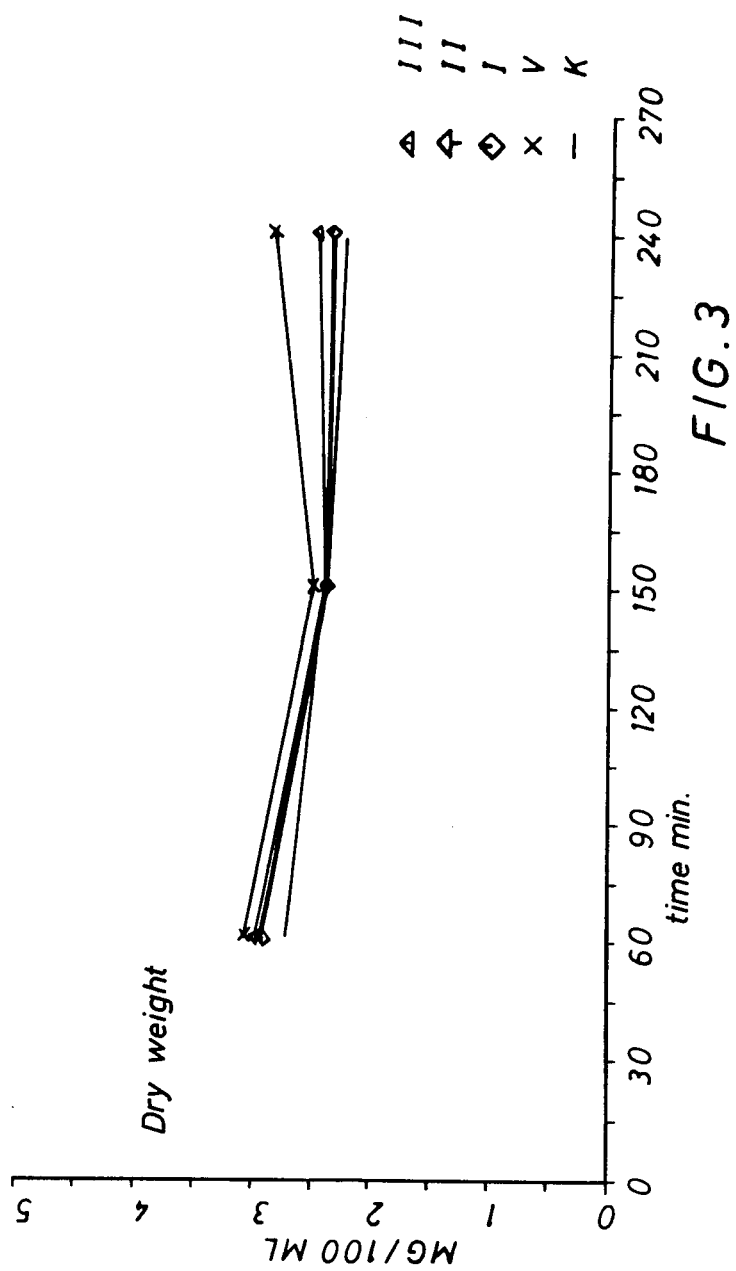

Finally, FIG. 3 gives the measurements for the dry weight. These show no important differences between the test groups and the control group.

In comparison with other, clinically tested, choleretics, cis-(3,3,5)-Trimethylcyclohexanol exhibited the potential effect described below. The choleretic effect of the substances named below was tested on male Wistar rats as follows: Rats under barbiturate anaesthesia, drainage of the Ductus hepaticus and collection of bile every 30 minutes, administration of the substances orally after a preliminary period of one hour. Reference: corrected basic secretion of the control animals which received a placebo.

Figure 4:
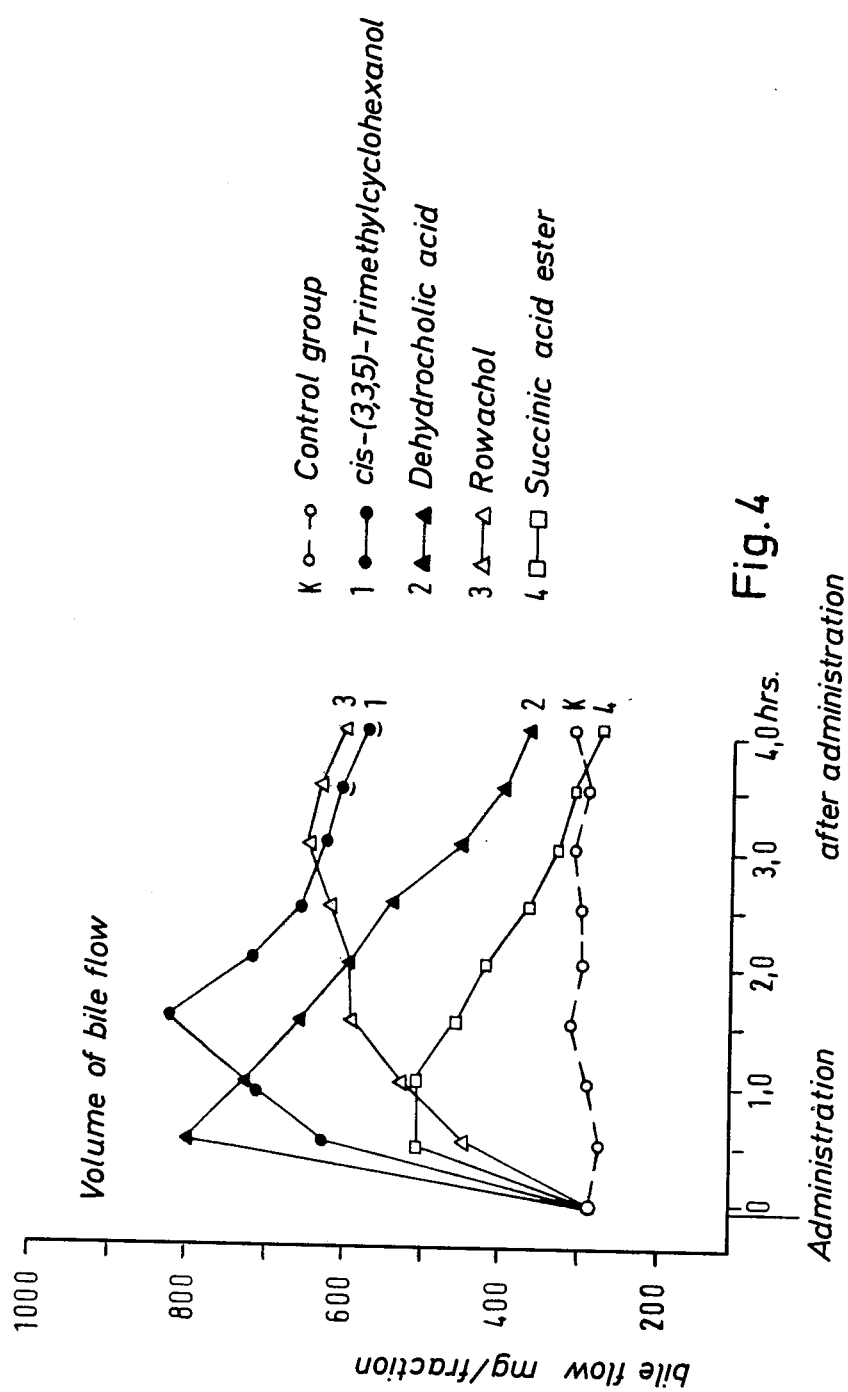

Test Substances:

Rowachol[R], Terpene mixture of 6 individual terpenes (the active ingredient per capsule of Rowachol ® is a mixture of the following terpene compounds: menthone 0.008953g, borneol 0.007462g, pinene 0.025372g, camphor 0.007462g, cineol 0.002983g and menthol 0.047768g) Dose 4.0 ml/kg Decholin[R], Dehydrocholic acid Dose 600 mg/kg Felogen[R], Succinic acid-mono-α-(2,5-endomethylene-$\Delta^3$-cyclohexenyl-ethyl ester Dose 100 mg/kg cis-(3,3,5)-Trimethylcyclohexanol    Dose 0.3 ml/kg The results of the test are illustrated in a graph in FIG. 4.

The succinic acid ester produced a distinct increase of choleresis which reached its maximum within one hour of application.

The choleretic effect then decreased gradually until the end of the experiment.

ROWACHOL, on the contrary, took longer to produce a choleretic effect, not reaching its maximum until within the third hour after administration. The effect then persisted for an appreciable period.

Dehydrocholic acid produced a very distinct increase of bile acid secretion, immediately after application and reached its maximum effect after 30 minutes. Following this, its choleretic action fell to some extent.

cis-(3,3,5)-Trimethylcyclohexanol, in a similar way, produced a great increase in choleresis immediately after application and its effect surpassed that of all the other test substances. The maximum secretion of bile was attained between the 1st and 2nd hour; the secretion of bile remained greatly increased until the end of the test. It is of particular interest that the small does of cis-(3,3,5)-Trimethylcyclohexanol was sufficient to achieve the effect described.

All the tested substances had a distinct choleretic action. With the dosages used in the test, cis-(3,3,5)-Trimethylcyclohexanol exhibited the most distinct choleretic effect, which was characterized by:

(a) a rapid commencement of the effect (b) persistence of the effect (c) a small dosage It must be pointed out that cis-(3,3,5)-Trimethylcyclohexanol in a dose of 0.3 ml/kg had a better choleretic effect than ROWACHOL in a dose of 4.0 ml/kg. As against ROWACHOL, which is a mixture of 6 terpenes, the subject of the invention has the advantage of being a single substance. It is of particular interest that the toxicity of cis-(3,3,5)-Trimethylcyclohexanol is not higher in a corresponding degree.

Toxicity tests of the substance were carried out on male and female rats. The tests were made in accordance with the recommendations of the "Appraisal of the safety of Chemicals in Foods, Drugs and Cosmetics" by the staff of the Division of Pharmacology, FDA, 1959. The test substance, slightly warmed and in fluid consistency, was administered to the animals once only orally by means of a rigid stomach tube. Under these test conditions the following results were obtained for male rats:

1. The $LD_{50}$ for 24 hours was determined as being 3.40 ml/kg and corresponded with the 7-day $LD_{50}$, since no later deaths occurred.
2. On the basis of the inclination factor S, the fluctuation range of acute toxicity could be well demarcated.

The results of the tests on female rats are as follows:

1. The $LD_{50}$ for 24 hours was determined as being 2.50 ml/kg. The 7-day $LD_{50}$ was 2.40 ml/kg.
2. On the basis of the inclination factor S, the fluctuation range of acute toxicity could be well demarcated.

It hence follows that the substance which is the subject of the invention is extremely well tolerated. In conjunction with the choleretic effect described above cis-(3,3,5)-Trimethylcyclohexanol therefore represents an advancement in this field of medicine.

The inventors consider the following to be the best method of application:

| Each enteric coated capsule will contain: | | |
|---|---|---|
| cis-(3,3,5)-Trimethylcyclohexanol | | 40.0 mg. |
| Excipient (Miglyol 812) | | 60.0 mg. |
| a neutral oil consisting of a | Total | 100.0 mg. |
| mixture of triglycerides of saturated vegetable fatty acids of medium chain length, $C_8$ to $C_{12}$ | | |
| Size of capsule: | 3 minims round | |
| Weight of capsule shell: | 75 mg. | |
| Composition of capsule shell: | Gelatine U.S.P., DAB | 70% |
| | Glycerine DAB | 30% |

The gelatine shell is preserved with 0.3% p-hydroxy-benzoic-acid ethyl-ester sodium. (Extra Pharmacopoeia Martindale, Vol. I) and 0.15% p-hydroxy-benzoic-acid propyl-ester sodium.

These capsules are for per-oral administration. It is recommended that the dosage would be one capsule three times daily. Due to the excellent tolerance to the active substance the ingestion may be continued indefinitely.

We claim:

1. A method for increasing choleresis in animals which comprises administering to an animal in need of such treatment a cholereticly effective amount of cis-3,3,5-trimethylcyclohexanol.
2. The method as defined in claim 1 which is a method for increasing the flow of bile and reducing the cholesterol level in the bile.
3. The method as defined in claim 1 which comprises orally administering cis-3,3,5-trimethylcyclohexanol in enteric coated capsules.

* * * * *